(12) United States Patent
Roberts et al.

(10) Patent No.: US 7,935,935 B2
(45) Date of Patent: May 3, 2011

(54) RADIATION-BASED TIMER FOR IMPLANTABLE MEDICAL DEVICES

(75) Inventors: Jonathan P. Roberts, Coon Rapids, MN (US); James D. Reinke, Maple Grove, MN (US); Jeffrey D. Wilkinson, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 162 days.

(21) Appl. No.: 12/394,179

(22) Filed: Feb. 27, 2009

(65) Prior Publication Data

US 2010/0219351 A1 Sep. 2, 2010

(51) Int. Cl.
*G01J 1/42* (2006.01)
(52) U.S. Cl. ......................................... 250/393
(58) Field of Classification Search .................. 250/393
See application file for complete search history.

(56) References Cited

U.S. PATENT DOCUMENTS

| | | | |
|---|---|---|---|
| 3,629,582 A | 12/1971 | Koehler et al. | |
| 3,836,798 A | 9/1974 | Greatbatch | |
| 4,275,405 A | 6/1981 | Shannon | |
| 4,676,661 A | 6/1987 | Keenan et al. | |
| 4,835,433 A | 5/1989 | Brown | |
| 5,180,917 A | 1/1993 | Wraight | |
| 5,646,409 A | 7/1997 | Leisinger et al. | |
| 6,849,845 B2 | 2/2005 | Lauffenburger | |
| 7,148,484 B2 | 12/2006 | Craig et al. | |
| 7,191,013 B1 * | 3/2007 | Miranda et al. | 607/60 |
| 7,657,297 B2 * | 2/2010 | Simpson et al. | 600/347 |
| 2004/0206916 A1 * | 10/2004 | Colvin et al. | 250/458.1 |
| 2005/0245799 A1 * | 11/2005 | Brauker et al. | 600/347 |
| 2005/0251033 A1 * | 11/2005 | Scarantino et al. | 600/436 |
| 2007/0249944 A1 | 10/2007 | Fischell et al. | |

FOREIGN PATENT DOCUMENTS

| | | |
|---|---|---|
| EP | 1508841 A2 | 2/2005 |
| WO | WO0146655 | 6/2001 |
| WO | WO2006077520 | 7/2006 |

OTHER PUBLICATIONS

J.P. Blanchard et al., "Radioisotope power for MEMS devices", Transactions of the American Nuclear Society, vol. 86, pp. 186-187, 2002.
J.P. Blanchard et al., "Radioisotope power for MEMS devices", Transactions of the American Nuclear Society, vol. 84, pp. 87-88, 2000.

(Continued)

*Primary Examiner* — David P Porta
*Assistant Examiner* — Djura Malevic
(74) *Attorney, Agent, or Firm* — Stephen W. Bauer; Michael J. Ostrom

(57) ABSTRACT

A radiation-based timer for use in an implantable medical device (IMD) includes a radiation source and a radiation detection circuit. The radiation source emits radiation particles during a process referred to as radioactive decay. The radiation detection circuit detects the radiation particles emitted during the decay process and tracks the number of radiation particles detected. When the number of radiation particles detected reaches a threshold value, a timer signal is generated. In this manner, the radiation-based timer generates a timer signal as a function of the radioactive decay of the radiation source. The timer signal may be used by one or more components of the IMD for any of a number of functions, including as a wakeup trigger for a communications and/or a sensor event.

33 Claims, 10 Drawing Sheets

OTHER PUBLICATIONS

L. Hui et al., "Self-reciprocating radioisotope-powered cantilever", Journal of Applied Physics, vol. 92, pp. 1122-1127, 2002.

Milenkovic et al., "Wireless sensor networks for personal health monitoring: Issues and an implementation", Elsevier 2006, 13 pages.

Shnayder et al., "Sensor Networks for Medical Care", Technical Report, Div of Engineering and Applied Sciences, Harvard University, 2005, 14 pages.

(PCT/US10/023719) PCT Notification of Transmittal of the International Search Report and the Written Opinion of the International Searching Authority, 12 pages.

Shankar Radhakrishnan et al., "Radioactive Counting Clocks," International Frequency Control Symposium and Exposition, 2006 IEEE, PI, Jun. 1, 2006, pp. 307-311.

* cited by examiner

RADIATION-BASED TIMER FOR IMPLANTABLE MEDICAL DEVICES

TECHNICAL FIELD

The disclosure relates generally to implantable medical devices and, in particular, to a timer mechanism of an implantable medical device.

BACKGROUND

A wide variety of implantable medical devices (IMDs) that deliver a therapy or monitor a physiologic condition of a patient have been clinically implanted or proposed for clinical implantation in patients. In some instances, IMDs may provide the capability to monitor a physiological condition of a patient, such as pressure, electrocardiogram (ECG), oxygen level or the like. In such cases the IMDs may or may not provide therapy to the patient. If therapy is delivered to the patient in addition to monitoring the physiological condicition, the IMDs may include a therapy module that delivers therapy to a variety of organs, nerves, muscles or tissues of the patients, such as the heart, brain, stomach, spinal cord, pelvic floor, or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, defibrillation or cardiac resynchronization via electrodes of one or more implantable leads. As another example, a neurostimulator may deliver electrical therapy signals, such as pulses, to a spinal cord, brain, pelvic floor or the like to alleviate pain or treat symptoms of any of a number of neurological or other diseases, such as epilepsy, gastroparesis, Alzheimer's, depression, obesity, incontinence and the like.

IMDs may also deliver, in addition to or instead of electrical stimulation therapy, drug therapy. For example, the IMD may deliver a drug or other therapeutic agent to the patient to treat pain or other symptoms of the condition of the patient. For example, the IMD may deliver morphine to an intrathecal location to treat pain. As another example, the IMD may deliver chemotherapy for the treatment of cancer. An IMD that delivers a drug or other therapeutic agent may sometimes be referred to as a drug pump or drug delivery device.

IMDs include a telemetry module that may exchange communications with a programming device (sometimes referred to as a programmer). For example, the IMDs may transmit information related to a condition of a patient, such as physiological signals measured by one or more sensors, or information related to a therapy delivered to the patient. This information may be previously stored or real-time information. The IMDs may also receive information from the programmer, such as configuration information that may be used to configure a therapy to be provided to the patient.

The various components of the IMDs, including the therapy module and the telemetry module, receive power from a power source. The power source may, in some instances, be a battery that has a limited service life. The service life of the battery may vary greatly based on the type of therapy provided to the patient. The service life of the battery, however, is typically on the order of several to tens of years.

To extend the life of the power source, the various components may periodically power up to perform a function and power down when not performing a function. The various components periodically power up and power down in accordance with a timer, such as a crystal oscillator. For example, a telemetry module may periodically power up in accordance with the timer to transmit or receive communications. As another example, a sensing module may periodically wake up based on the timer to sense a physiological signal of the patient.

SUMMARY

In general, this disclosure relates to disclosure relates to a radiation-based timer for use in an implantable medical device (IMD). In one example, this disclosure is directed to an implantable medical device comprising a radiation-based timer and at least one other component that uses a timer signal of the generated by the radiation-based timer to perform a function. The radiation-based timer includes a radiation source that emits radiation particles during radioactive decay, at least one radiation detection element capable of detecting radiation particles and a counter that tracks a number of radiation particles detected by the at least one radiation detection element. The radiation-based timer generates a timer signal upon the number of detected radiation particles exceeding a threshold value.

In another example, this disclosure is directed to a method comprising detecting, with at least one radiation detection element, radiation particles emitted from a radiation source of a radiation-based timer during radioactive decay, tracking a number of radiation particles detected by the at least one radiation detection element and generating a timer signal upon the number of detected radiation particles exceeding a threshold value.

In a further example, this disclosure is directed to an implantable medical device comprising means for detecting radiation particles emitted from a radiation source of a radiation-based timer during radioactive decay, means for tracking a number of radiation particles detected by the at least one radiation detection element and means for generating a timer signal upon the number of detected radiation particles exceeding a threshold value.

This summary is intended to provide an overview of the subject matter described in this disclosure. It is not intended to provide an exclusive or exhaustive explanation of the techniques described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

This disclosure relates to a radiation-based timer for use in an implantable medical device (IMD). The radiation-based timer includes a radiation source, e.g., a radioactive element, and a radiation detection circuit. The radiation source emits radiation particles (sometimes referred to as ionizing particles) during a process referred to as radioactive decay. The radiation detection circuit detects the radiation particles emitted during the decay process and tracks the number of radiation particles detected. When the number of radiation particles detected reaches a threshold value, a timer signal is generated. In this manner, the radiation-based timer generates a timer signal as a function of the radioactive decay of the radiation source. The timer signal may be used for any of a number of functions, such as for a wakeup trigger for performing a receive function, a transmit function, a sense function, a therapy delivery function, a self-test function, a patient alert function or other function.

Figure 1:
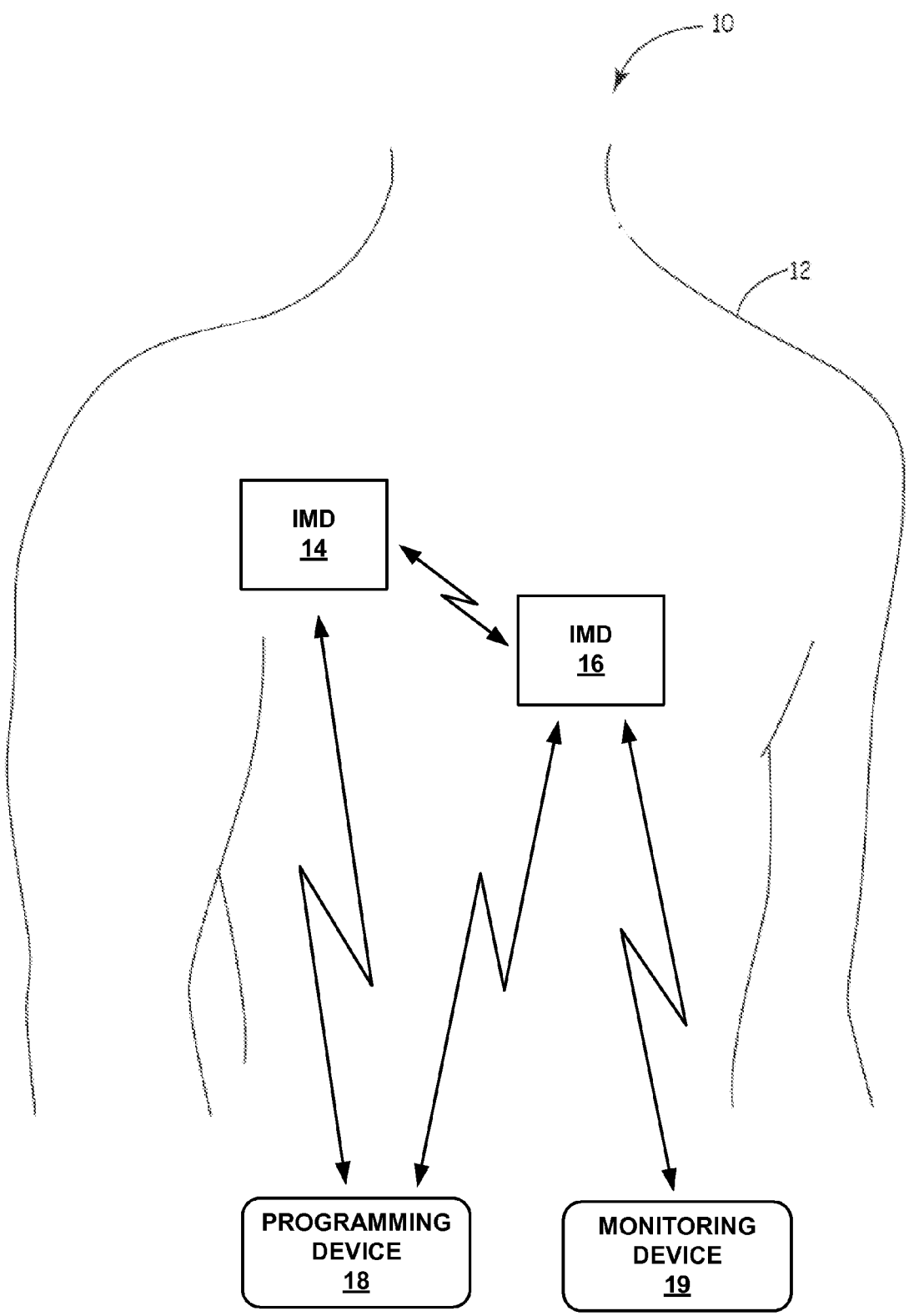
FIG. 1 is a conceptual diagram illustrating an example medical system in which at least one device uses the radiation-based timer described in this disclosure.

FIG. 1 is a conceptual diagram illustrating an example medical system 10 in which at least one device uses the radiation-based timer described in this disclosure. Medical system 10 includes one or more medical devices that may be used to provide therapy to and/or sense one or more physiological signals of a patient 12. Patient 12 ordinarily, but not necessarily, will be a human.

In the example illustrated in FIG. 1, medical system 10 includes an IMD 14, IMD 16, programming device 18 and monitoring device 19. Medical system 10 may, however, include more or fewer medical devices that may or may not be implanted within patient 12. Although described in the context of implantable medical devices, the techniques of this disclosure may be used in medical devices that are not implanted within patient 12. For example, the techniques may be used within medical devices worn or otherwise attached to or carried by patient 12.

IMD 16 may be any of a variety of medical devices. As one example, IMD 16 may be a wireless sensor implanted within patient 12 to sense one or more physiological signals of patient 12. IMD 16 may be implanted at targeted monitoring sites and transmit the sensed signals, thus avoiding limitations associated with lead-based sensors. In some instances, IMD 16 uses the sensed physiological signals to monitor a condition of patient 12 or provide therapy to patient 12 as a function of the sensed physiological signals. Alternatively, or additionally, IMD 16 transmits the sensed physiological signals to another device, such as IMD 14, programming device 18 or monitoring device 19, which may in turn monitor the condition of patient 12 or provide therapy to patient 12 as a function of the sensed physiological signals. IMD 16 may sense, sample, and process one or more physiological signals such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter.

Although IMD 16 is described with reference to FIG. 1 as being a wireless sensor, IMD 16 may be any of a variety of other medical devices that deliver therapy, sense physiological signals or both. For example, IMD 16 may be a leadless pacer (sometimes referred to as a wireless pacer). Other examples of medical devices that IMD 16 could be include therapy delivery devices, such as electrical stimulation devices that deliver electrical stimulation to a heart, brain, spinal cord, stomach, pelvic floor or other location within or on patient 12, or drug pumps or infusion pumps that delivers a drug, therapeutic agent, saline solution, or other liquid to locations within patient 12.

IMD 16 includes a power source that provides power to the various components of IMD 16. Because the power source of IMD is typically limited, some or all of the components of IMD 16 may enter a low power state to reduce power consumption when not performing functions attributed to the component. The low power state may, for example, be a "SLEEP state" in which the component uses substantially less power than when operating in a normal operating state or an "OFF state" in which the only power consumed by the component is due to leakage current. For example, the component may consume at least approximately 80% less power in the low power state, and more preferable at least approximately 90% less power.

One such power intensive component of IMD 16 that may enter the low power state from time to time is a transceiver. The power demands of continuously operating the transceiver may result in a quicker depletion of the power source of IMD 16. As such, IMD 16 may interleave intervals during which the transceiver is placed into a low power state (e.g., SLEEP state or OFF state) with intervals during which the transceiver is powered up for transmitting and/or receiving communications. This process is sometimes referred to as duty cycling of the transceiver. The transceiver may be periodically woken up from the low power state to listen for a transmission from another device or transmit information to another device, e.g., one of devices 14, 18 or 19.

Other components or, in some cases, all of the components of IMD 16 may periodically be placed in a respective low power state. For example, a sensing module of IMD 16, which may include an amplifier and other circuitry, may enter the low power state from time to time to reduce power consumption. The sensing module of IMD 16 may be periodically woken up from the low power state to sense a physiological signal of patient 12, thus reducing the average power consumption of IMD 16 used for sensing.

IMD 16 includes a radiation-based timer that generates a timer signal. The radiation-based timer includes a radiation source (e.g., radioactive element) that emits radiation particles during a process called radioactive decay. The radiation-based timer also includes a radiation detection circuit that detects the radiation particles emitted during the radioactive decay of the radiation source. The radiation-based timer generates a timer signal based on the number of radiation particles detected. The timer signal may be used for periodically waking up components of IMD 16 from their respective low power states. For example, the timer signal from the radiation-based timer may be used to wake up a transceiver to look for communications from or transmit communications to another device, wake up a sensing element to monitor a physiological parameter or function, or wake up a therapy module to deliver a therapy. IMD 16 may, however, use the radiation-based timer signal for any of a number of other functions, such as a timer for performing self-testing to ensure proper function, as a watchdog timer to determine whether the device entered an unwanted state, to activate certain therapies at certain times of day, as a real-time clock feature used to time stamp when certain events occur, or any other function.

IMD 16 may be communicatively coupled with other medical devices implanted within or worn by or attached to patient 12 to form a local area network, sometimes referred to as a body area network (BAN) or personal area network (PAN). For example, IMD 16 may be communicatively coupled with IMD 14 as well as any additional implantable medical devices within patient 12. Monitoring device 19 and/or programming device 18 may be included within the BAN, e.g., in instances in which devices 18 or 19 are portable devices worn by, carried by or attached to patient 12 or otherwise located at a close distance to patient 12. The local network including devices 14, 16, 18 and/or 19 may operate in accordance with any of a number of network topologies, including a star network, ring network, tree network, mesh network, fully connected network or any other network topology. Each device may therefore be enabled to communicate wirelessly along multiple pathways with each of the other networked devices. As such, devices 14, 16, 18 and 19 may represent a distributed system of implantable medical devices that cooperate to monitor a condition of patient 12.

IMD 14 may be any of a variety of medical devices that provide therapy to patient 12, sense physiological conditions of patient 12 or a combination thereof. In some instances, IMD 14 may be a device that provides electrical stimulation therapy in the form of cardiac rhythm management therapy to a heart of patient 12. In such a case, IMD 14 may include one or more implantable leads with one or more electrodes that extend from IMD 14 for delivering therapy to and/or sensing physiological signals of patient 12. The leads may be implanted within one or more atria or ventricles of the heart of patient 12 or a combination thereof. In other words, IMD 14 may be used for single chamber or multi-chamber cardiac rhythm management therapy. The cardiac rhythm management therapy delivered by IMD 14 may include, for example, pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like to treat various conditions, including movement and affective disorders such as chronic pain, Parkinson's disease, tremor and dystonia, urinary storage and voiding dysfunction, digestion dysfunction, sexual dysfunction or the like.

Like IMD 16, some or all of the components of IMD 14 may enter a low power state to reduce power consumption when not performing functions attributed to the component. These components may periodically wake up from the low power state to perform their prescribed function in accordance with a timer signal provided by a radiation-based timer within IMD 14.

Programming device 18 may be a dedicated hardware device with dedicated software for programming of IMDs 14 and/or 16. Alternatively, programming device 18 may be an off-the-shelf computing device running an application that enables programming device 18 to program IMDs 14 and/or 16. In some examples, programming device 18 may be a handheld computing device that may be attached to or otherwise carried by patient 12. Alternatively, programming device 18 may be a computer workstation. Programming device 18 may include a user interface that receives input from the user and/or displays data to the user, thus allowing the user to program the therapy delivered by IMDs 14 and 16 or display data received from IMDs 14 and 16.

Monitoring device 19 may be a dedicated hardware device with dedicated software for receiving communications from IMDs 14 and/or 16 or an off-the-shelf computing device running an application that enables monitoring device 19 to receive communications from IMD 22. In some examples, monitoring device 19 may be a handheld computing device that may be attached to or otherwise carried by patient 12. Alternatively, monitoring device 19 may be a computer workstation, e.g., such as a CareLink® monitor, available from Medtronic, Inc. of Minneapolis, Minn. Monitoring device 19 may include a user interface that receives input from the user and/or displays data to the user, thus allowing the user to program the therapy delivered by IMDs 14 and 16 or display data received from IMDs 14 and 16.

In some instances, programming device 18 and/or monitoring device 19 may upload data retrieved from IMDs 14 and/or 16 to a remote server, from which a clinician or another user may access the data to determine whether a potential sensing integrity issue exists or whether the measured physiological parameter values indicate patient 12 requires medical attention. An example of a remote server includes the CareLink® Network, available from Medtronic, Inc. of Minneapolis, Minn.

Figure 2:
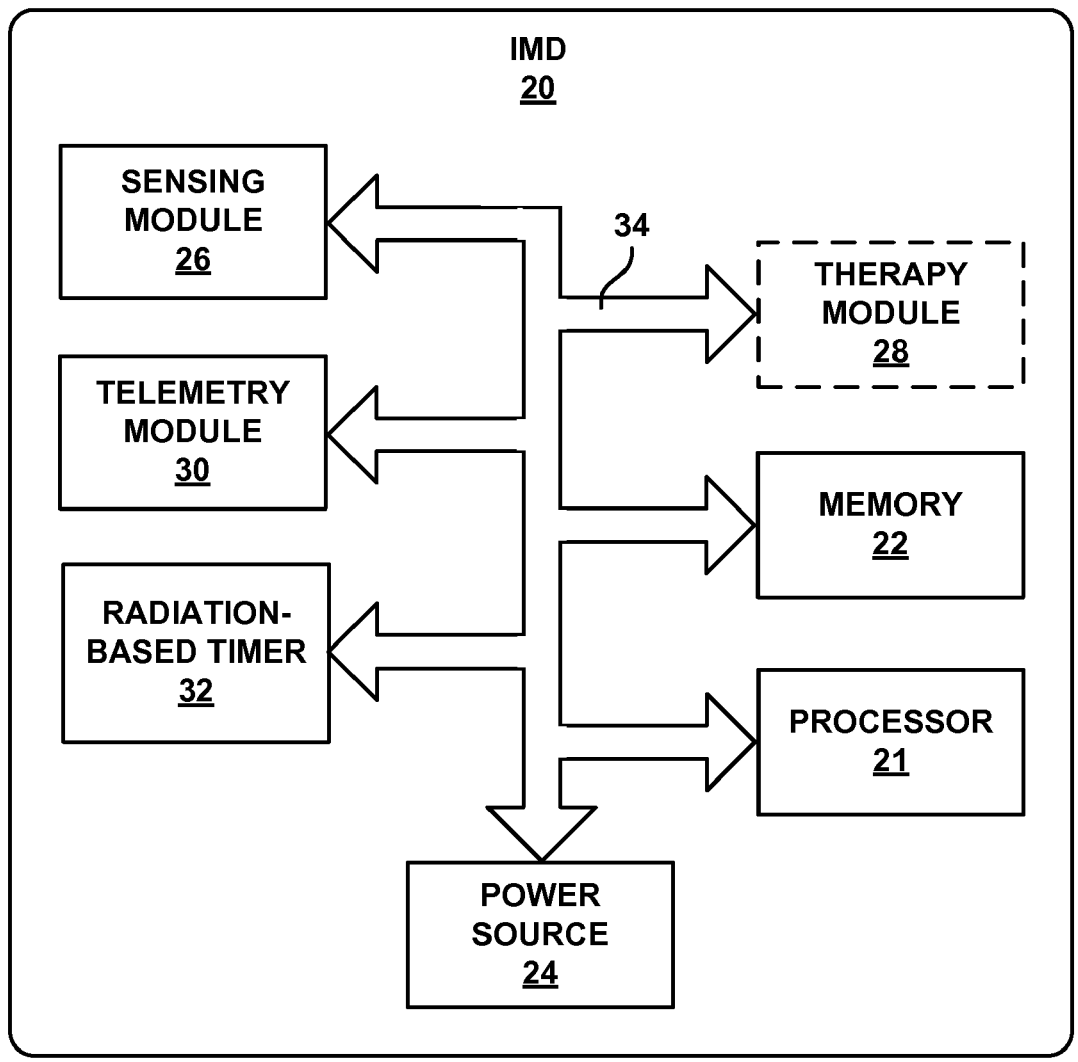
FIG. 2 is a functional block diagram of an example configuration of components of an implantable medical device of the medical system of FIG. 1.

FIG. 2 is a functional block diagram of an example configuration of components of IMD 20. IMD 20 may, for example, be one of IMDs 14 or 16 of FIG. 1. In the example illustrated in FIG. 2, IMD 20 includes a processor 21, memory 22, power source 24, sensing module 26, telemetry module 30 and radiation-based timer 32. IMD 20 may, in some instances, also include a therapy module 28, shown in phantom lines. The various components of IMD 20 are interconnected by a data bus 34. In other examples, the various components of IMD 20 may be interconnected by a number of point-to-point connections.

Processor 21 may include one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 21 may include multiple components, such as any combination of one or more microprocessors, one or more controllers, one or more DSPs, one or more ASICs, or one or more FPGAs, as well as other discrete or integrated logic circuitry. The functions attributed to processor 21 herein may be embodied as software, firmware, hardware or any combination thereof.

Memory 22 may include computer-readable instructions that, when executed by processor 21, cause components of IMD 20 to perform various functions attributed to the respective components in this disclosure. Memory 22 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 20 are coupled to power source 24, which may include a non-rechargeable battery, rechargeable storage device such as a rechargeable battery or capacitor (which may be recharged internally or transcutaneously with the use of electromagnetic or piezoelectric transformers), energy-harvesting device, or a combination thereof. A non-rechargeable battery may be capable of holding a charge for several years, while a rechargeable battery may be inductively charged from an external device, e.g., on a daily or weekly basis. Power source 24 also may include power supply circuitry for providing regulated voltage and/or current levels to power the components of IMD 20.

Sensing module 26 is configured to monitor one or more physiological signals using one or more sensors connected to sensing module 26. The one or more sensors may be housed within IMD 20 or located outside IMD 20. In some instances, the housing or can of IMD 20 may function as the sensor. In one example, sensing module 26 is configured to monitor signals sensed by one or more of electrodes on leads extending from IMD 20. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter. Such sensors may include, for example, one or more electrodes, accelerometers, gyroscopes, pressure sensors, optical sensors, piezoelectric sensors, pulse oximeters, or any other physical sensor. The one or more sensors coupled to sensing module 26 may be passive or active sensors.

Sensing module 26 may store the sensed signals in memory 22. In some instances, sensing module 26 may store the sensed signals in raw form. In other instances, sensing module 26 may process the sensed signals and store the processed signals in memory 22. For example, sensing module 26 may amplify and filter the sensed signal and store the filtered signal in memory 22. The signals stored by sensing module 26 may, in some cases, be retrieved and further processed by processor 21. Additionally, processor 21 may control telemetry module 30 to send the signals stored by sensing module 26 to another device, such as IMD 14, programming device 18 or monitoring device 19 of FIG. 1.

Under the control of processor 21, telemetry module 30 may receive data from and send data to programming device 18 with the aid of an antenna, which may be internal and/or external to IMD 20. Telemetry module 30 includes any suitable hardware, firmware, software or any combination thereof for communicating with another device. For example, telemetry module 30 may include appropriate modulation, demodulation, frequency conversion, filtering, and amplifier components for transmission and reception of data.

Because power source 24 is typically limited, some or all of the components of IMD 20 may enter a low power state (e.g., SLEEP state or OFF state) when not performing functions attributed to the component in an effort to reduce power consumption. For example, telemetry module 30, which includes transmit and/or receive circuitry, may be placed into a low power state from time to time. While in the low power state, power may not be delivered to the one or more amplifiers, modulators, demodulators, filters, or other circuitry of telemetry module 30. Telemetry module 30 may periodically wake up from the low power state to listen for a transmission from another device or transmit information to another device, e.g., one of devices 14, 18 or 19 of FIG. 1.

In addition to or instead of telemetry module 30, sensing module 26 may be placed into a low power state from time to time. While in the low power state, power may not be delivered to the one or more sensors, amplifiers, filters, or other circuitry of sensing module 26. Sensing module 26 may periodically wake up from the low power state to sense a physiological signal. In the case of continuous blood glucose monitoring, sensing module 26 may wake up from the low power state every few minutes to monitor the blood glucose level of patient 12. Other components or, in some cases, all of the components of IMD 20 except the radiation-based timer 32 may operate in a similar manner.

Radiation-based timer 32 generates a timer signal, e.g., for use in waking up one or more of the components of IMD 20, e.g., telemetry module 30 and/or sensing module 26, from their respective low power states. Radiation-based timer 32 includes a radiation source that emits radiation particles during radioactive decay. Radioactive decay refers to the process in which an unstable atomic nucleus loses energy by emitting radiation particles (sometimes referred to as ionizing particles). The decay of a single atom may be referred to as a decay event. On the atomic level, radioactive decay is a random process in that it is difficult to determine when a given atom of the radiation source will decay. However, the rate at which the radiation source decays, on average, is predictable over a large number of atoms.

Because the radioactive decay is predictable over a large number of atoms, radiation-based timer 32 may generate a timer signal as a function of the amount of radioactive decay. To do so, radiation-based timer 32 includes a radiation detection circuit that detects radiation particles emitted during the decay events and tracks the number of radiation particles detected. The radiation detection circuit may include one or more detection elements capable of detecting radiation. The detection elements may be any semiconductor device such as a diode or field effect transistor. The semiconductor device may be formed from silicon (Si), silicon carbide (SiC), Gallium arsenide (GaAs), Gallium phosphide (GaP), Gallium Nitride (GaN) or other bandgap material. These elements may be discrete sensors or incorporated directly into circuit elements such as inverters or storage cells. In one example, the output of the detection elements may be fed to a counter or logic that functions as a counter to track the number of radiation particles detected. In another example, the output of detection elements may be fed to an integrator that integrates the signal to track the number of radiation particles detected. Details of these examples are provided in more detail below.

Radiation-based timer 32 generates a timer signal based on the number of radiation particles detected. For example, radiation-based timer 32 may maintain a counter that is preset to a value and decremented when a radiation particle is detected by one of the detection elements. Alternatively, the counter may be decremented when a particular number radiation particles are detected, e.g., after radiation particles are detected by all or a portion of the detection elements. Radiation-based timer 32 generates the timer signal upon expiration of the counter. In other words, radiation-based timer 32 generates the timer signal upon detecting a threshold number of radiation particles. The timer signal may, in some instances, be used as a wakeup trigger to periodically wakeup one or more components of IMD 20, such as telemetry module 30 or sensing module 26.

The number of radiation particles emitted by the radiation source per unit of time is proportional to the quantity of the radioactive element or elements that make up the radiation source. Thus, the larger the quantity of the radioactive element making up the radiation source, the larger the number of particles emitted per unit of time. As the radioactive element decays over time, the radiation source emits a smaller number of radiation particles per unit of time. In some instances, the radiation element selected as the radiation source has a half-life sufficient to produce a predictable count, and thus a substantially periodic timer signal, over the life of IMD 20. The half-life of the radiation source refers to the interval required for the quantity of the radiation source to decay to half of its initial value. Radioactive isotopes that have suitable half-lives include $^3$He (tritium) with a half-life of approximately 12.32 years and $^{63}$Ni with a half-life of approximately 100.1 years. Radioactive elements or compounds with a mixed decay series such as uranium with a half life of approximately 4.47 billion years and thorium with a half life of approximately 14 billion years may also be used.

In other instances, radiation-based timer 32 may adjust the threshold count value as the radiation source decays such that the timer signal is substantially periodic over the lifetime of IMD 20. For example, the threshold count value may be decreased as a function of time based on the half-life of the radiation element of the radiation source. Compensating the threshold count value based on the half-life of the radiation source may be necessary for radioactive isotopes or compounds having half-lives that are less than approximately 10 years. The smaller the half-life of the radiation source the more likely compensation may be necessary.

Radiation-based timer 32 may adjust the threshold count value in any of variety of ways. In one instance, radiation-based timer 32 may decrement the threshold count value over time. At each interval, for example, radiation-based timer 32 computes a count adjustment value (Δcount) that is equal to:

$$\Delta\text{count} = \text{thresh} * \ln(2) * x / \text{half\_life},$$

where thresh is the threshold count value, ln( ) is a natural log function, x is equal to the interval or period of the timer signal, and half_life is the half-life of the radiation source. For a radiation timer that has an interval of 1 second and a radiation source with a half-life of 8 years (4,204,800 seconds), count adjustment value (Δcount) is equal to 0.000000165*thresh. Since this is smaller than one, radiation-based timer 32 accumulates the Δcount's until it reaches a value of one and then decrements the threshold count value by one.

In instances in which multiple detector elements are used (as described in further detail below), radiation-based timer 32 may activate switches or other mechanisms to adjust the number of detector elements used to detect radiation particles. For example, radiation-based timer 32 may decrease the number of detector elements utilized in the similar manner to decrementing the threshold count value described above to provide a compensation for the decrease in emitted radiation over time.

Radiation-based timer 32 may be actively timed to a clock of a second device. When IMD 20 is communicating with a second device, such as programming device 18, monitoring device 19 or another IMD that has a continuous running clock (e.g., crystal oscillator), radiation-based timer 32 may adjust the threshold count value based on a difference between when the timer signal occurs and an expected event time (e.g., when the event occurs in the second device). If the timer signal of radiation-based timer 32 is earlier than expected, the threshold count value is increased and if the timer signal of radiation-based timer 32 is later than expected, the threshold count value is decreased.

When used as a wakeup trigger, the timer signal should have a low enough variation to meet a wakeup window specification of a communication protocol. The standard deviation ($\sigma$) of a timer signal upon detecting N radiation particles is well approximated by square root of N.

$$\sigma = \sqrt{N}$$

For a timer signal with an accuracy of ±10% (i.e., 1 standard deviation), radiation-based timer 32 should detect 100 radiation particles before generating the timer signal. For a timer signal with an accuracy of ±5%, radiation-based timer 32 should detect 400 radiation particles before generating the timer signal. Thus, the accuracy of the timer signal is equal to:

$$\text{Accuracy} = \frac{\sqrt{N}}{N}$$

The accuracy of the timer signal may, therefore, also be adjusted by adjusting the threshold number of detected radiation particles. In accordance with the equation above, increasing the threshold count may increase the accuracy of the timer signal because of the increased predictability of radioactive decay over larger numbers of atoms. Additionally, radiation-based timer 32 consumes less power than conventional timing mechanisms, such as crystal oscillators. The radioactive decay of radioactive elements is also independent of temperature at temperatures typically experienced by patient 12.

IMD 20 may sometimes be placed within an environment in which it is exposed to an external radiation source. IMD 20 may be exposed to an external radiation source when patient 12 undergoes any of a variety of medical procedures, including radiography (e.g., X-ray), computed tomography (CT) scans, nuclear medicine imaging, radiation treatment or the like. IMD 20 may also be exposed to an external radiation source in a non-medical environment. When exposed to such external radiation sources, the detection elements of radiation-based timer 32 may detect radiation particles emitted from the external radiation source in addition to the radiation particles emitted from the radiation source of radiation-based timer 32. The detection elements of radiation-based timer 32 may be uncapable of distinguishing between the radiation particles emitted from the external radiation source and the radiation source of radiation-based timer 32. As such, the detection of the radiation particles from the external radiation source may result in the counter expiring sooner than desired, which in turn may cause an inadvertent or false timer signal. The inadvertent or false timer signal may cause the frequency of the timer signal to no longer meet a wakeup window specification when used as a wakeup trigger for components of IMD 20. Alternatively or additionally, the inadvertent timer signal may cause the wakeup time of the components of IMD 20 to be unsynchronized with another device, e.g., devices 14, 18 and 19.

To reduce the likelihood of an inadvertent or false timer signal, radiation-based timer 32 may include a radiation shield that shields the radiation detection circuit from the external radiation source. The shield also protects patient 12 or other circuitry of IMD 20 from being exposed to the internal radiation source. Alternatively, or additionally, radiation-based timer 32 may include an external radiation detection element for detecting external radiation. The external radiation detection element is placed in a location at which it is unlikely to detect radiation particles from the radiation source of radiation-based timer 32. The location of the external radiation detection element is also placed in close enough proximity to the internal radiation detection element(s) such that when the internal radiation detection elements detect the external radiation source so does the external radiation detection element.

Radiation-based timer 32 may adjust the counter to account for the external radiation detected by the external radiation detection element. For example, when the counter is decremented from a threshold value to zero, radiation-based timer 32 increments the counter each time the external radiation detection element detects a radiation particle, as the radiation particle is presumably from the external radiation source. In this manner, radiation-based timer 32 may discriminate the number of radiation particles associated with the radiation source of radiation-based timer 32 from the number of radiation particles associated with the external radiation source, thereby mitigating against false or inadvertent timer signals. As another example, radiation-based timer 32 may maintain a second counter that tracks the number of times the external radiation detection element detects a radiation particle and subtract the value of the second counter from the first counter. Radiation-based timer 32 may then use the result of the subtraction for generating the timer signal, e.g., by generating the timer signal when the result of the subtraction reaches the threshold value.

In some instances, radiation-based timer 32 may harvest and store power associated with the radioactive decay of the radiation source. Radiation-based timer 32 may, for example, include a power storage device (e.g., capacitor or rechargeable battery) that stores the power associated with the radiation particles. The power storage device of radiation-based timer 32 may be used to power the components of radiation-based timer 32, thus providing a completely self-sufficient timer 32. In other instances, radiation-based timer 32 may harvest the power of the radiation particles and store the power in power source 24.

As described above, in some instances, IMD 20 may deliver therapy to patient 12 in addition to sensing physiological parameters. In this case, IMD 20 includes a therapy module 28 that, under the control of processor 21, delivers therapy to patient 12. In the case of electrical stimulation therapy, therapy module 28 may generate an electrical stimulation signal and deliver the stimulation to patient 12, e.g., via one or more electrodes. Processor 21 controls therapy module 28 to deliver electrical stimulation signals, e.g., pacing pulses, resynchronization pulses and/or cardioversion-defibrillation shocks in the case of cardiac rhythm management therapy, with amplitudes, pulse widths, frequencies, electrode combinations or electrode polarities specified by a selected therapy program. Therapy module 28 may deliver one or more of these types of stimulation in the form of other signals besides pulses or shocks, such as sine waves, square waves, or other substantially continuous signals. In other instances, IMD 20 may provide therapy to patient 12, but not perform sensing. Instead, IMD 20 may receive sensed parameters from other devices implanted within or worn by patient 12. As such, IMD 20 may only provide sensing, only deliver therapy or provide sensing and therapy. One or more of the timing mechanisms of therapy module 28 may use the timer signal generated by radiation-based timer 32. For example, therapy module 28 uses the timer signal of radiation-based timer 32 to track escape intervals, refractory periods, blanking intervals, or the like.

Figure 3:
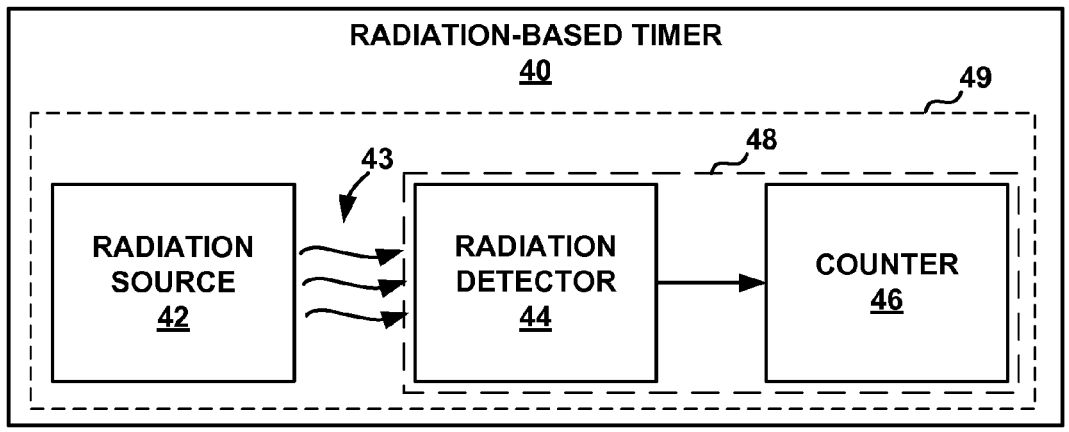
FIG. 3 is a block diagram illustrating an example radiation-based timer that generates a timer signal in accordance with the techniques of this disclosure.

FIG. 3 is a block diagram illustrating an example radiation-based timer 40 that generates a timer signal in accordance with the techniques of this disclosure. The timer signal may, for example, be used to trigger one or more components of IMD 20 to wakeup from a low power state. Radiation-based timer 40 may correspond with radiation-based timer 32 of IMD 20 (FIG. 2). Radiation-based timer 40 includes a radiation source 42, a radiation detector 44 and a counter 46. Radiation detector 44 and counter 46 may together constitute a radiation detection circuit 48.

Radiation source 42 is a material that emits radiation particles during radioactive decay. The radiation particles are represented by lines 43 in FIG. 3. The radiation particles emitted by radiation source 42 may be alpha particles, beta particles or gamma particles, depending on the radioactive element or elements making up radiation source 42. Radiation source 42 may include, for example, tritium, uranium, thorium or any other suitable radioactive isotope or compound.

Radiation source 42 may be placed on an integrated circuit in close proximity to radiation detection circuit 48. In one example, radiation source 42 is placed in intimate contact with radiation detector 44. In another example, radiation source 42 may be placed such that there is a small separation between radiation source 42 and radiation detector 44, e.g., less than 1 millimeter (mm). In this case, the intervening space between radiation source 42 and radiation detector 44 would be either vacuum or gas. Radiation detector 44 detects the radiation particles emitted during the decay of radiation source 42. Radiation detector 44 may include one or more detection elements, such as one or more photodiodes, inverters or any other semiconductor device, that detect radiation particles emitted during the decay of radiation source 42. Each of the detection elements may be capable of detecting a single radiation particle.

Counter 46 tracks the number of radiation particles detected by radiation detector 44. In one example, counter 46 may be preset to a threshold value and decrement when a radiation particle is detected by one of the detection elements or radiation detector 44. In this manner, counter 46 may be decremented in response to detecting each radiation particle. Alternatively, counter 46 may be decremented when a particular number of radiation particles are detected. For example, counter 46 may be decremented when all or a portion of the detection elements of radiation detector 44 have detected radiation particles. In this manner, counter 46 is not decremented upon detecting each radiation particle, but only after detecting N radiation particles, where N is any integer greater than or equal to zero. Although described above as a counter that counts downward, the counter may instead be an up counter that increments until it reaches a threshold value. Counter 46 may be a digital counter or an analog counter, e.g., an integrator.

Radiation-based timer 40 may generate a timer signal upon expiration of counter 46, e.g., when the timer reaches zero, or upon counter 46 reaching a threshold value. In this manner, radiation-based timer 40 may generate the timer signal upon detecting a threshold number of radiation particles. Because radioactive decay of the radiation source is, on average, predictable, radiation-based timer 40 may be substantially periodic. As such, the timer signal may be used by IMD 20 as a wakeup trigger to periodically wakeup one or more components of IMD 20, such as telemetry module 30 or sensing module 26, from a low power state. The timer signal may, however, be used for other purposes, such as wake up a therapy module to deliver a therapy, timer for performing self-testing to ensure proper function, as a watchdog timer to determine whether the device entered an unwanted state, or any other function.

The frequency of the timer signal may be adjustable to suit a particular application. The frequency of the timer signal may need to meet a wakeup window specification of a communication protocol. For example, the frequency of the timer signal may be set to wakeup telemetry module 30 every few seconds to transmit and/or receive data. As another example, the frequency of the timer signal may be set to wakeup sensing module 26 every few minutes to sense a physiological signal of patient 12. The frequency of the time signal may be dynamically adjusted by changing the threshold value of counter 46. For example, increasing the threshold count may decrease the frequency of the timer signal. Furthermore, as described above, radiation-based timer 40 may adjust the threshold count value as the radiation source decays such that the timer signal is substantially periodic over the lifetime of IMD 20. For example, the threshold count value may be decreased as a function of time based on the half-life of the radiation element of the radiation source.

Radiation-based timer 40 may also include a radiation shield 49. Radiation shield 49 shields the components of radiation-based timer 40, including radiation source 42, radiation detector 44 and counter 46, from an external radiation source. As such, radiation detector 44 is less likely to detect radiation particles emitted from the external radiation source, thus reducing the likelihood of inadvertent or false timer signals. Additionally, radiation shield 49 may shield other components of IMD 20 and/or patient 12 from radiation particles emitted by radiation source 42. Radiation shield 49 may be made from one or more materials that shield radiation, such as lead, tungsten, bismuth, copper, titanium, and zinc. In some instances, radiation shield 49 may only shield a portion of the components of radiation-based timer 40, e.g., only radiation source 42 and radiation detector 44. In other instances, radiation-based timer 40 may not include radiation shield 49 at all. Radiation source 42 may, for example, be such a small amount of radioactive material that no shielding is necessary.

Figure 4:
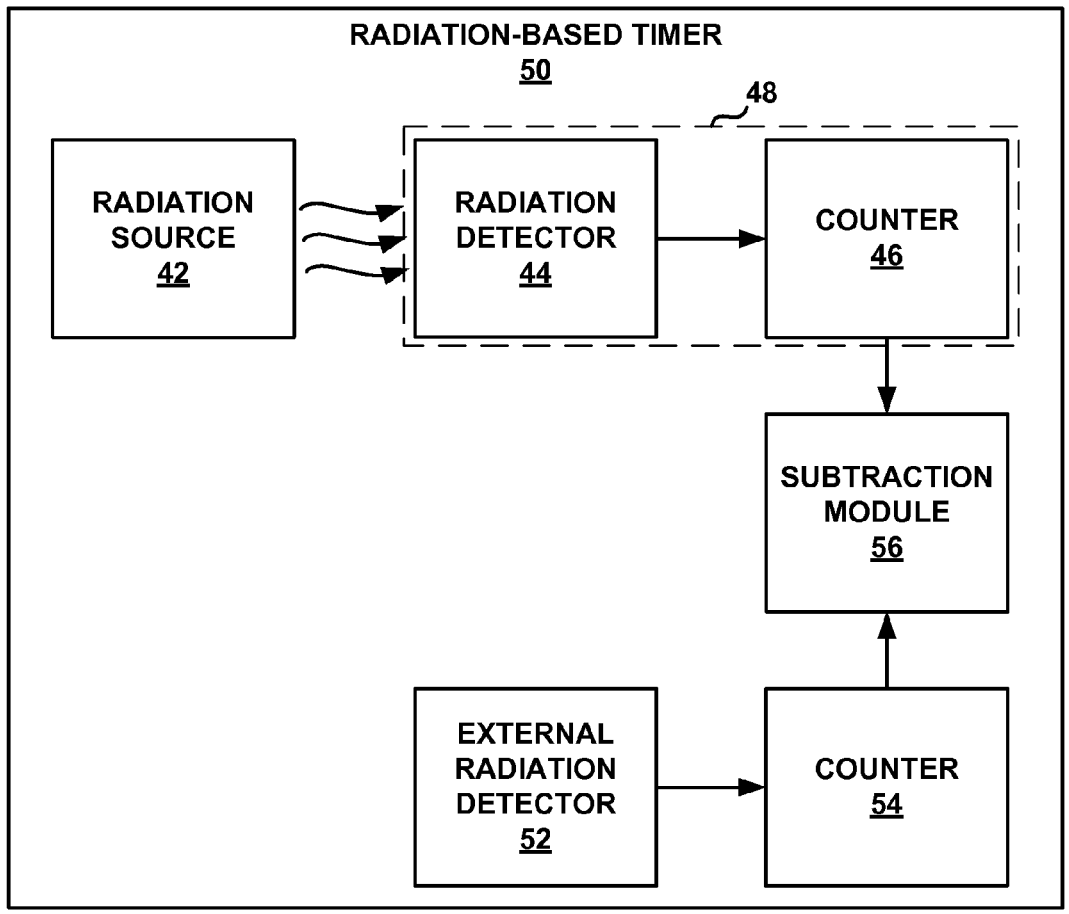
FIG. 4 is a block diagram illustrating another example radiation-based timer that generates a timer signal.

FIG. 4 is a block diagram illustrating another example radiation-based timer 50 that generates a timer signal. The timer signal may, for example, be used to trigger one or more components of IMD 20 to wakeup from a low power state. Radiation-based timer 50 may correspond with radiation-based timer 32 of IMD 20 (FIG. 2). Radiation-based timer 50 includes a radiation source 42, radiation detector 44 and counter 46. Radiation detector 44 and counter 46 may together constitute a radiation detection circuit 48. Radiation source 42, radiation detector 44 and counter 46 operate in the same manner as described above with respect to FIG. 3 and will therefore not be described further here.

As described above, IMD 20 may sometimes be placed within an environment in which it is exposed to an external source of radiation, such as when patient 12 undergoes any of a variety of medical procedures including radiography (e.g., X-ray), computed tomography (CT) scans, nuclear medicine imaging, radiation treatment or the like, or in non-medical environments. When exposed to such external radiation sources, detection elements of radiation detector 44 may detect radiation particles emitted from the external radiation source in addition to the radiation particles emitted from radiation source 42. Radiation detector 44 may be unable to distinguish between the radiation particles emitted from the external radiation source and radiation source 42 of radiation-based timer 32. As such, the detection of the radiation particles from the external radiation source may result in the counter expiring sooner than desired, which in turn may cause an inadvertent or false timer signal.

To reduce the likelihood of inadvertent or false timer signals, radiation-based timer 50 includes an external radiation detector 52, counter 54 and subtraction module 56. External radiation detector 52 may, in some instances, be substantially similar to radiation detector 44. As such, external radiation detector 52 may include one or more detection elements, such as one or more photodiodes, inverters or any other semiconductor device, that detect radiation particles emitted during radioactive decay. External radiation detector 52 is placed in a location at which it is unlikely to detect radiation particles from radiation source 42. As such, any radiation detected by external radiation detector 52 is attributed to the external radiation source.

Counter 54 tracks the number of radiation particles detected by external radiation detector 52. Counter 54 may be a digital counter or an analog counter, such as an integrator. Subtraction module 56 determines a difference between the value of counter 46 and the value of counter 54. This difference, i.e., the result of the subtraction, is determined to be the number of detected radiation particles that are attributable to radiation source 42. As such, the timer signal may be generated as a function of the difference between the value of counter 46 and the value of counter 54. In this manner, radiation-based timer 40 may discriminate the number of radiation particles associated with the radiation source of radiation-based timer 40 from the number of radiation particles associated with the external radiation source, thereby mitigating against false or inadvertent timer signals.

In other instances, external radiation detector 52 and counter 54 may be used to determine the reliability of the timer signal generated by radiation-based timer 50. In other words, radiation-based timer 50 may use external radiation detector 52 and counter 54 to determine when the timer signal is unreliable, e.g., when counter 54 exceeds a threshold value, due to exposure to an external radiation source. In response to determining that the timer signal of radiation-based timer 50 is unreliable, the components of the IMD that are normally in the low power state may be powered up continuously (e.g., with no low power state intervals) to ensure that no event, such as a sense event or telemetry event, is missed. Alternatively, the components of the IMD may be held in the low power state, in which case, resynchronization of the component would need to be re-established. In this case, the timer signal is essentially ignored. In a further example, the components of the IMD may use a secondary clock circuit as a timer signal while the IMD is exposed to the radiation source. The secondary clock circuit may be a higher power clock source that is not influenced by the external radiation source, such as a crystal oscillator. The components of the IMD may return to using the clock signal of radiation-based timer 50 once the IMD is no longer exposed to the external radiation source.

The arrangement of components in FIG. 4 is one example. In other instances, radiation-based timer 50 may not include a counter 54 and a subtraction module 56. Instead, counter 46 may be adjusted in the opposite manner when the external radiation detection element detects a radiation particle than when radiation detector 44 detects a radiation particle. For example, if counter 46 is decremented in response to radiation detector 44 detecting a radiation particle, counter 46 is incremented in response to external radiation detector 52 detecting a radiation particle.

Figure 5:
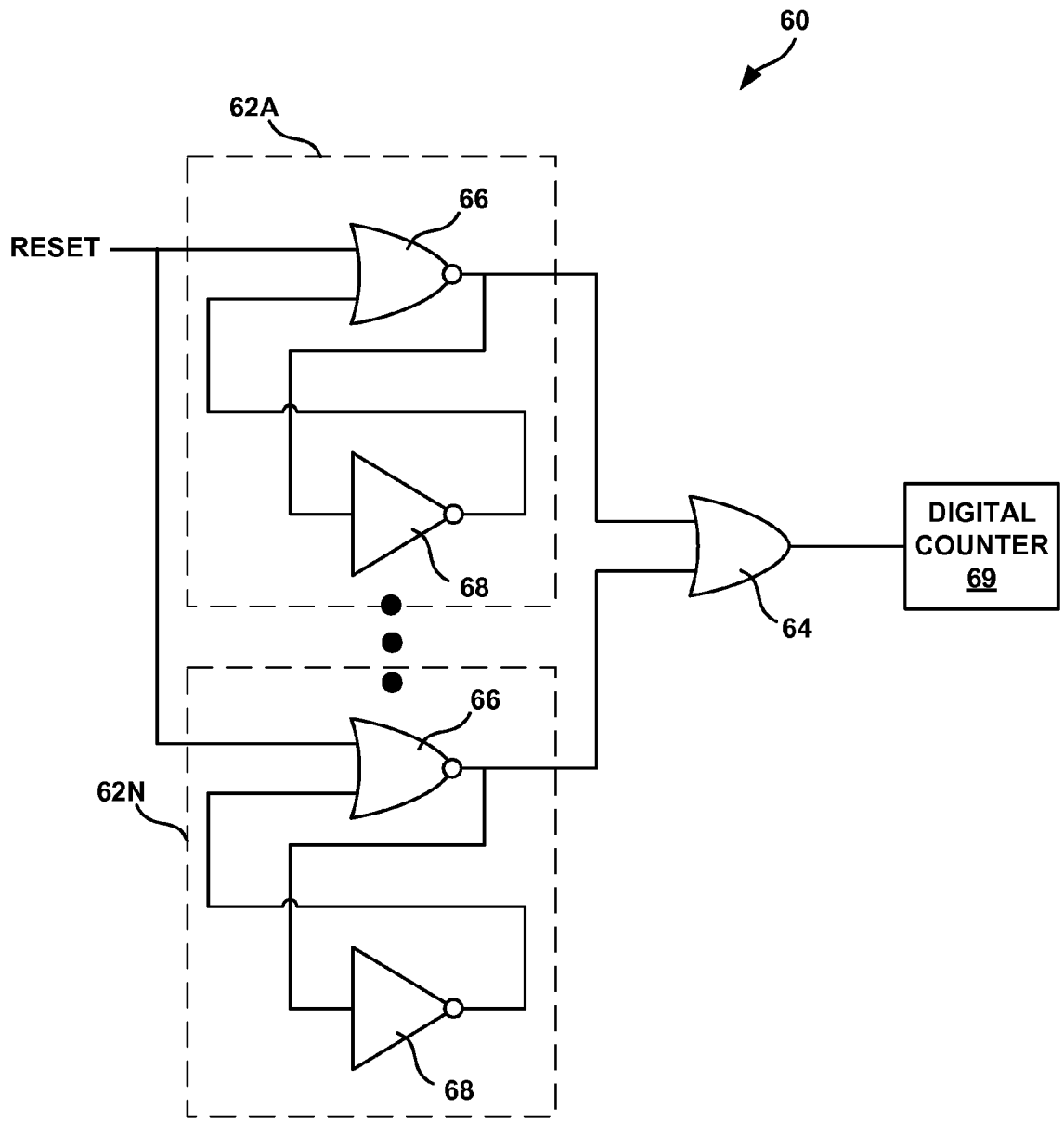
FIG. 5 is a circuit diagram illustrating an example radiation detection circuit.

FIG. 5 is a circuit diagram illustrating an example radiation detection circuit 60. Radiation detection circuit 60 may correspond to radiation detection circuit 48 of FIGS. 3 and 4. Radiation detection circuit 60 includes detection elements 62A-62N (collectively "detection elements 62"). Radiation detection circuit 60 may include any number of detection elements 62, including only a single radiation detection element 62.

Detection elements 62 change states in response to detecting a radiation particle. In other words, the output of detection elements transitions from LOW to HIGH or from HIGH to LOW in response to detecting the radiation particle. In the example illustrated in FIG. 5, each of detection elements 62 includes a respective logical NOR gate 66 and inverter 68. NOR gate 66 is a logic gate outputs a HIGH output (1) if both the inputs to NOR gate 66 are LOW (0). If one or both inputs are HIGH (1), NOR gate 66 outputs a LOW output (0). NOR gate 66 has two inputs, one of which is connected to a reset line (labeled "RESET" in FIG. 5) and one that is connected to the output of inverter 68.

Inverter 68 outputs a voltage representing the opposite logic-level to its input. In other words, if the input of inverter 68 is HIGH, the output of inverter 68 is LOW and if the input of inverter 68 is LOW, the output of inverter 68 is HIGH. In the example illustrated in FIG. 4, the input of inverter 68 is connected to the output of NOR gate 66. Inverter 68 may, in one example, include a small area PMOS and a large area NMOS. The area may be optimized to ensure a particle will cause a detect, yet have as large an area of collection as possible. Due to its larger area, the NMOS area of inverter 68 is more likely to be impacted by a radiation particle compared to the other devices in the structure. Due to the large amount of carriers generated upon impact, the output of inverter 68 flips states upon being impacted by the radiation particle, which, in turn, causes the output of NOR gate 66 to flip states. In other words, the output of detection elements 62 change state when the respective inverter 68 is struck by a radiation particle. In this manner, detection elements 62 operate as latches that flip states in response to detecting radiation particles. Detection elements 62 may be reset to their initial state by a RESET signal, which in this example may be imposed after any of detection elements 62 detect a radiation particle.

OR gate 64 is a logic gate that outputs a HIGH output (1) if any of its inputs are HIGH and output a LOW output (0) if none of its inputs are HIGH. In the example illustrated in FIG. 4, the inputs of OR gate 64 are the outputs of detection elements 62. In instances in which there are more than two detection elements 62, radiation detection circuit 60 may include a plurality of cascaded OR gates instead of a single OR gate 64. In the example of FIG. 5, however, only a single OR gate is illustrated for ease of description. Alternatively, OR gate 64 may be an OR gate that includes more than two inputs.

The output of OR gate 64 is fed to a counter, such as digital counter 69. As described above, digital counter 69 may be incremented or decremented based on the output of OR gate 64. In the case of a down counter, digital counter 69 may be preset to a threshold value and decremented each time the output of logical OR gate 64 goes from LOW to HIGH. In the case of an up counter, digital counter 69 may be initiated at zero and incremented each time the output of the logical OR gate 64 goes from LOW to HIGH until digital counter 69 reaches a threshold value. In the example illustrated in FIG. 5, the output of logical OR gate 64 goes from LOW to HIGH each time one of the detection elements 62 detects a radiation particle. As such, digital counter 69 is adjusted (e.g., incremented or decremented) each time a radiation particle is detected.

The threshold value may be set to a value that represents the number of detected radiation particles needed to generate the desired time interval. As described above, the threshold value may be set based on the rate of radioactive decay of radiation source 42, desired frequency of the timer signal or the like. In some instances, the threshold value may dynamically change as a function of time in accordance with a half-life of radiation source 42 to account for the decrease in the number of radiation particles emitted from the smaller quantity of radioactive element during the decay.

The circuit illustrated and described in FIG. 5 is one example circuit and should not be considered limiting. The techniques of this disclosure may be implemented using a different arrangement of digital and/or analog components that generate an equivalent circuit to the one illustrated in FIG. 5.

Figure 6:
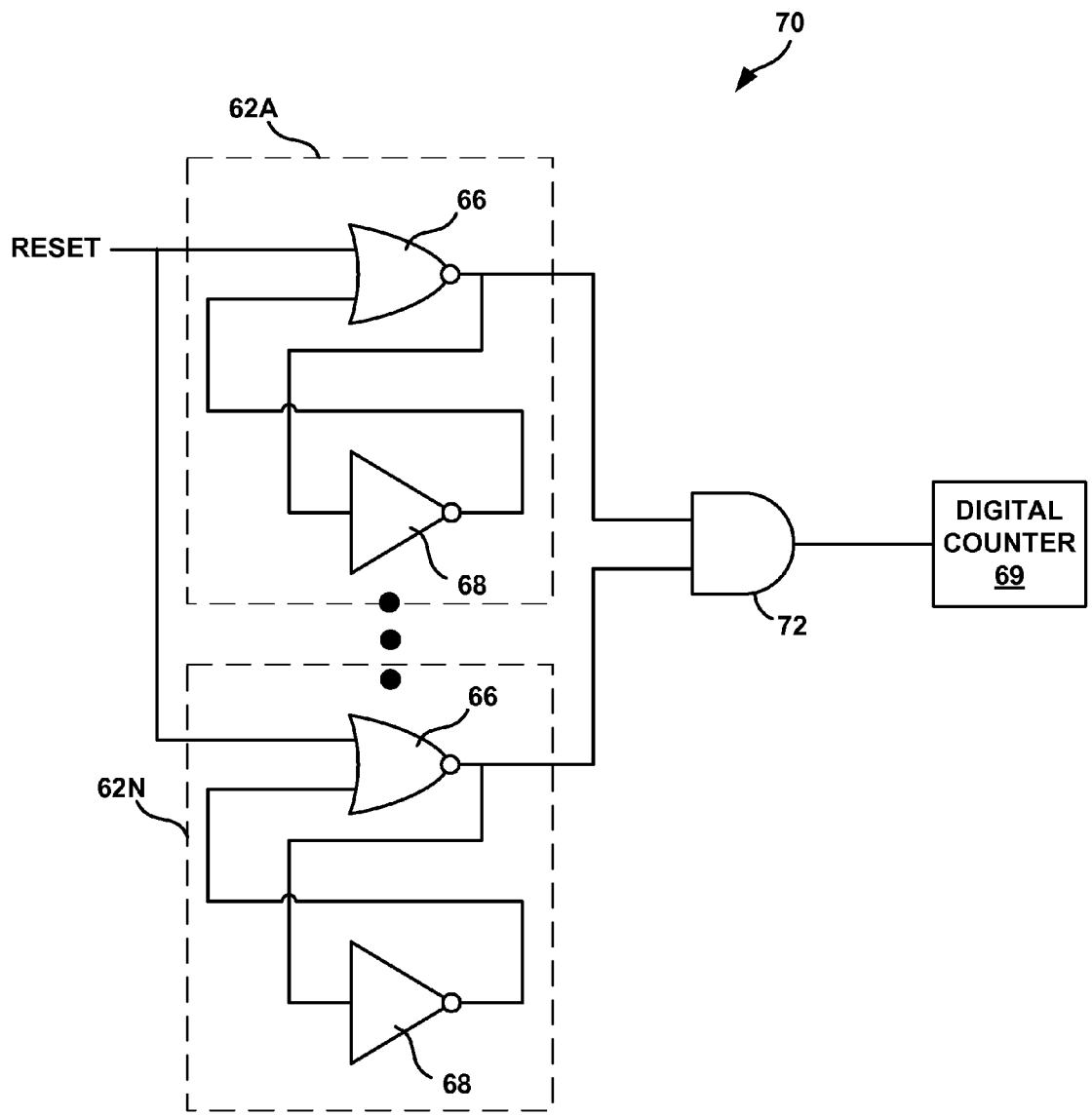
FIG. 6 is a circuit diagram illustrating another example radiation detection circuit.

FIG. 6 is a circuit diagram illustrating another example radiation detection circuit 70. Radiation detection circuit 70 of FIG. 6 is similar to radiation detection circuit 60 of FIG. 5, except that a logical AND gate 72 replaces logical OR gate 64. Like logical OR gate 64, the inputs of logical AND gate 72 are connected to outputs of the plurality of detection elements 62 and the output of logical AND gate 72 is fed to digital counter 69. The output of logical AND gate 72 goes from LOW to HIGH when all of radiation detection elements 62 detect a radiation particle. As such, digital counter 69 is only incremented or decremented after each and every radiation detection element 62 detects a radiation particle. In other words, counter 69 is decremented after N radiation particles are detected, where N is equal to the number of radiation detection elements 62. Likewise, each of radiation detection elements 62 is reset only upon all of radiation detection elements 62 detecting a radiation particle.

Adjusting digital counter 69 only after N radiation particles are detected results in less counter toggles needed to generate a given time interval. This may reduce the amount of power consumed by the radiation-based timer to perform the event count while still providing programmability. In other instances, digital counter 69 may be eliminated with AND gate 72 functioning as the counter. In this case, the radiation-based timer consumes no power to operate a counter element. The counter-less timer may be programmable by dynamically adjusting the number of detection elements 62 whose output feeds AND gate 72. The number of detection elements 62 feeding AND gate 72 may be adjusted using one or more switches.

In instances in which there are more than two detection elements 62, radiation detection circuit 70 may include a plurality of cascaded AND gates instead of a single AND gate 72. In the example of FIG. 5, however, only a single AND gate is illustrated for ease of description. Alternatively, AND gate 72 may be an AND gate that includes more than two inputs. The circuit illustrated and described in FIG. 6 is one example circuit and should not be considered limiting. The techniques of this disclosure may be implemented using a different arrangement of digital and/or analog components that generate an equivalent circuit to the one illustrated in FIG. 6.

Figure 7:
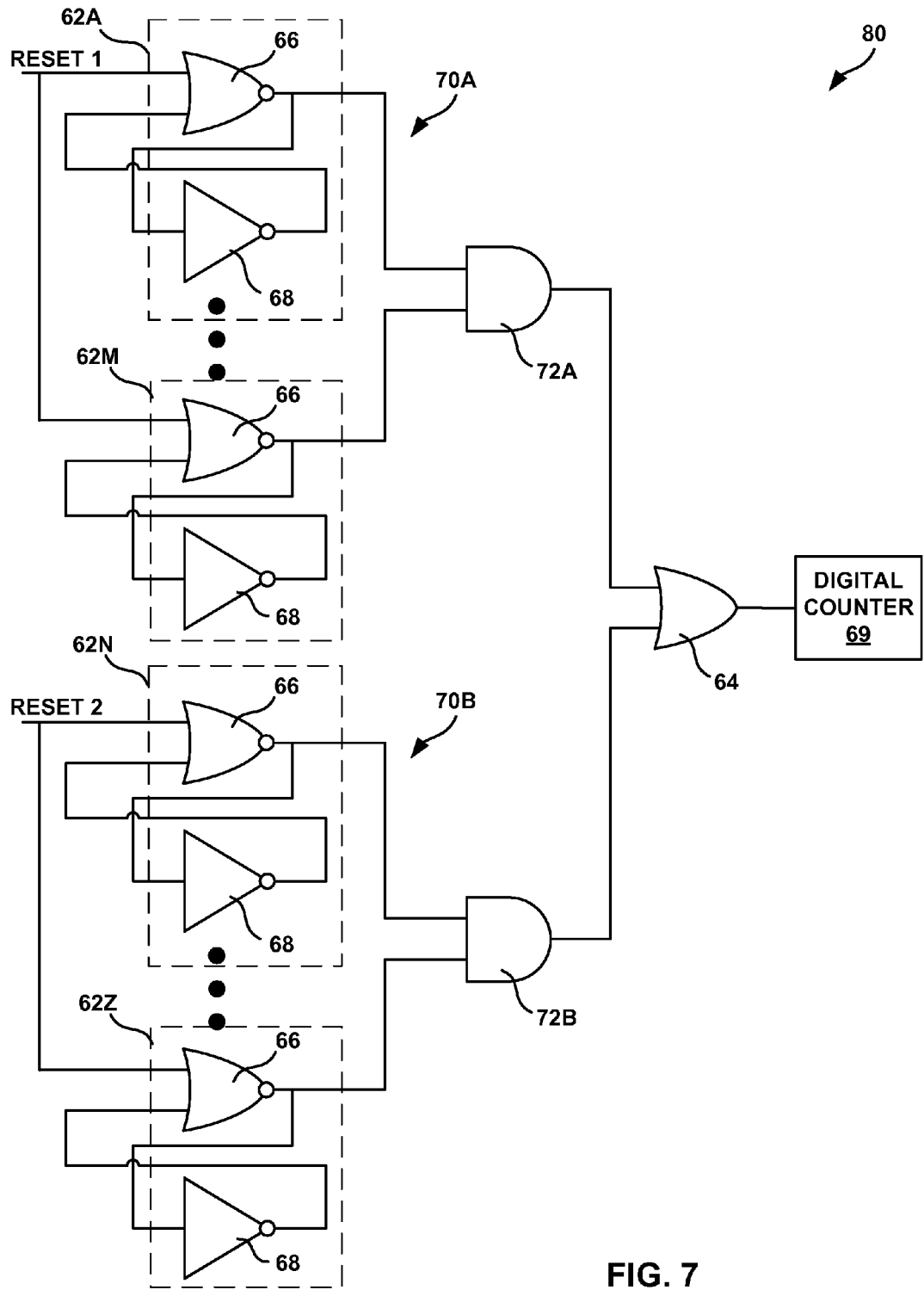
FIG. 7 is a circuit diagram illustrating a further example radiation detection circuit.

FIG. 7 is a circuit diagram illustrating another example radiation detection circuit 80. Radiation detection circuit 80 includes radiation detection circuits 70A and 70B that are substantially similar to radiation detection circuit 70 of FIG. 6. Radiation detection circuit 70A includes detection elements 62A-62M, the outputs of which feed to AND gate 72A. The output of AND gate 72A transitions from LOW to HIGH when all of detection elements 62A-62M detect an emitted radiation particle. After all of detection elements 62A-62M detect an emitted radiation particle, detection elements are reset via a reset signal RESET 1.

Radiation detection circuit 70B includes detection elements 62N-62Z, the outputs of which feed to AND gate 72B. The output of AND gate 72B transitions from LOW to HIGH when all of detection elements 62N-62Z detect an emitted radiation particle. After all of detection elements 62N-62Z detect an emitted radiation particle, detection elements are reset via a reset signal RESET 2. In some instances, the number of detection elements 62 in radiation detection circuits 70A and 70B is the same. In other instances, the number of detection elements 62 in radiation circuits 70A and 70B are different.

The outputs of the radiation detection circuits 70A and 70B, i.e., the outputs of AND gates 72A and 72B, respectively, are input to an OR gate 64. The output of the OR gate transitions from LOW to HIGH when all of detection elements 62 of either radiation detection circuit 70A or radiation detection circuit 70B detect radiation particles. The output of OR gate 64 increments or decrements digital counter 69 as described above. Radiation detection circuit 80 of FIG. 7 provides the flexibility of a programmable counter with a reduction in power consumption to perform the adjustment of digital counter 69 as the counter is not adjusted after each detection of a radiation particle. Although the OR gate 64 is coupled to two radiation detection circuits 70A and 70B in the example of FIG. 7, more than two radiation detection circuits 70 may have their outputs fed to OR gate 64.

Radiation detection circuits 60, 70 and 80 of FIGS. 5, 6 and 7, respectively, may be exposed to an external source of radiation that may cause the counter to expire sooner than desired, in turn causing an inadvertent or false timer signal. To reduce the likelihood of inadvertent or false timer signals, a second radiation detection circuit similar to those illustrated in FIGS. 5, 6, and 7 may be placed in a location at which it is unlikely to detect radiation particles from the internal radiation source, e.g., radiation source 42. As such, any radiation detected by the second radiation detection circuit is attributed to the external radiation source and is subtracted from the counter value of digital counter 69 to adjust the count value of digital counter 69 to account for external radiation particles detected.

Figure 8:
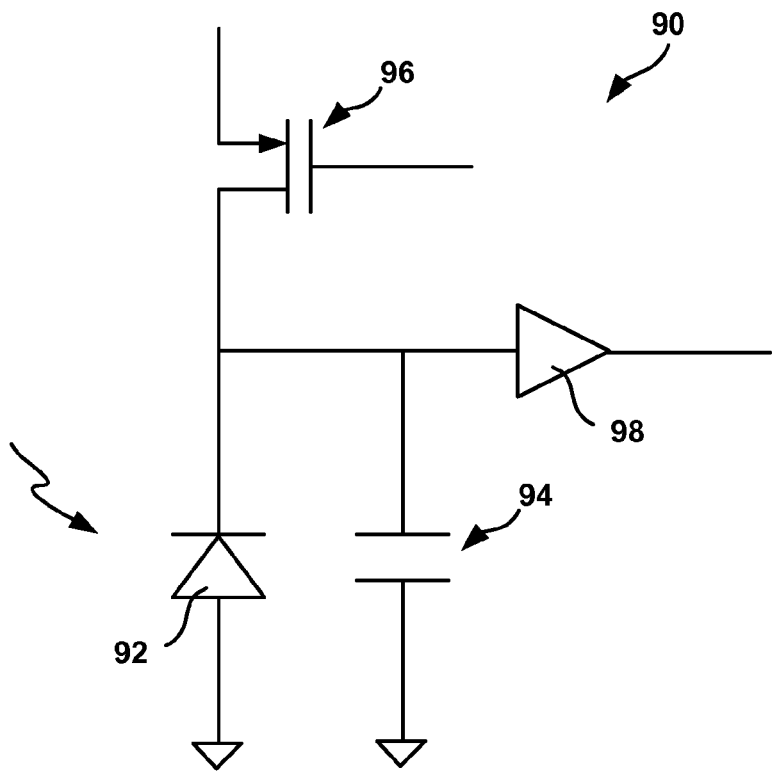
FIG. 8 is a circuit diagram illustrating another example radiation detection circuit.

FIG. 8 is a circuit diagram illustrating another example radiation detection circuit 90. Radiation detection circuit 90 includes a photodiode 92, a capacitor 94, a transistor 96 and an integrator 98. A cathode of photodiode 92 is coupled to a drain of transistor 96 and the anode of photodiode 92 is coupled to ground. The cathode of photodiode 92 is also coupled to integrator 98. The source of transistor 96 is coupled to a voltage (Vthreshold).

Photodiode 92 is also coupled in parallel with capacitor 94. Photodiode 92 may be optimized for detection of the expected radiation particles. A P/N junction depth, dopant type, and dopant and base material properties (e.g., purity, dopant level and dopant type) may be adjusted to achieve a desired sensitivity.

Figure 9:
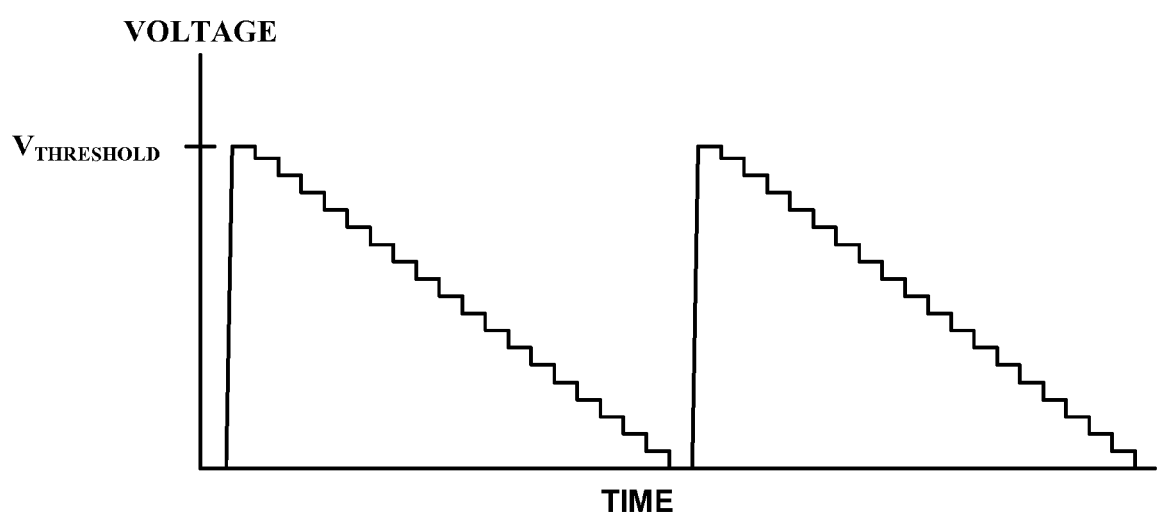
FIG. 9 is an example graph illustrating the accumulation of an integrator of the circuit of FIG. 8.

When transistor 96 turns on, a voltage waveform rises rapidly to a threshold voltage value ($V_{threshold}$) as illustrated in FIG. 9. When a radiation particle strikes photodiode 92, one or more electrons are excited within photodiode 92 producing a photocurrent. The photocurrent generated by photodiode begins to discharge capacitor 94. In other words, a voltage begins to drop on capacitor 94. As the photodiode continues to be struck by radiation particles emitted during the radioactive decay process of radiation source 42, the voltage on capacitor 94 continues to decrease.

At the same time, integrator 98 begins to accumulate the voltage increments created by the detected radiation particles. Integrator 98 incrementally decrements the output voltage, which starts at approximately $V_{threshold}$, by incremental voltages equal to voltage corresponding to the radiation particles until it reaches approximately zero. An example graph illustrating the output of integrator 98 is illustrated in FIG. 9. Each of the steps along the ramp portion of the output of integrator 98 represents an incremental voltage change (decrease) caused by detection of a radiation particle. In this manner, integrator 98 may be viewed as operating as an analog counter. Upon reaching approximately zero, transistor 96 operates as a switch to preset the voltage on capacitor 94 and photodiode 92 back to $V_{threshold}$.

The frequency of a timer signal output by integrator 98 may change as a function of the size of the photodiode, size of the capacitor, threshold voltage value, voltages applied to the gate and drain of transistor 96 or the like.

Figure 10:
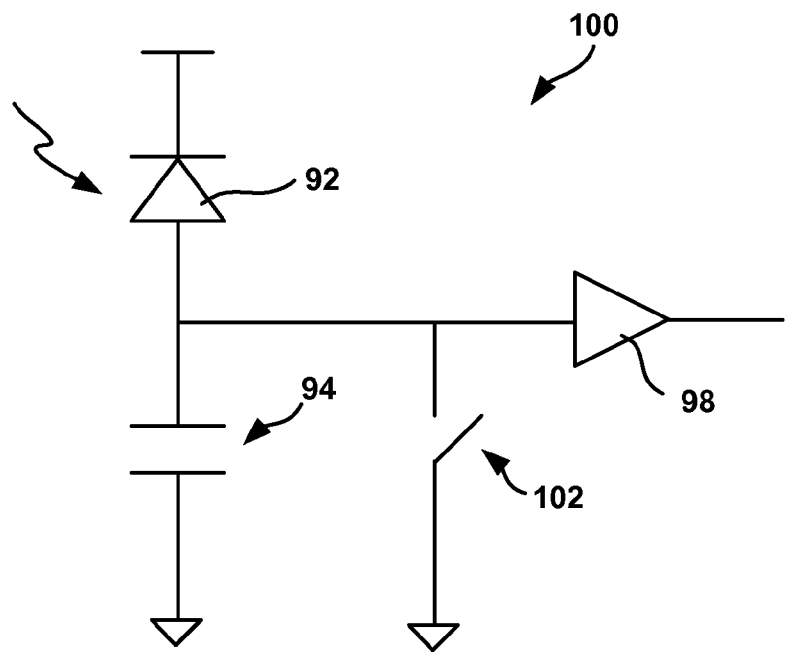
FIG. 10 is a circuit diagram illustrating an additional example radiation detection circuit.

FIG. 10 is block diagram illustrating a further example of a radiation detection circuit 100. Radiation detection circuit 100 includes a photodiode 92, a capacitor 94, an integrator 98 and a switch 102. Photodiode 92 is coupled in series to capacitor 94, with the anode of photodiode 92 being connected to capacitor 94. The anode of photodiode 92 is also connected to integrator 98. Capacitor 94 is connected in parallel with switch 102.

When a radiation particle strikes photodiode 92, one or more electrons are excited within photodiode 92 producing a photocurrent. The photocurrent generated by photodiode begins to charge capacitor 94. In other words, a voltage begins to build on capacitor 94. As the photodiode continues to be struck by radiation particles emitted during the radioactive decay process of radiation source 42, the voltage on capacitor 94 continues to build.

Figure 11:
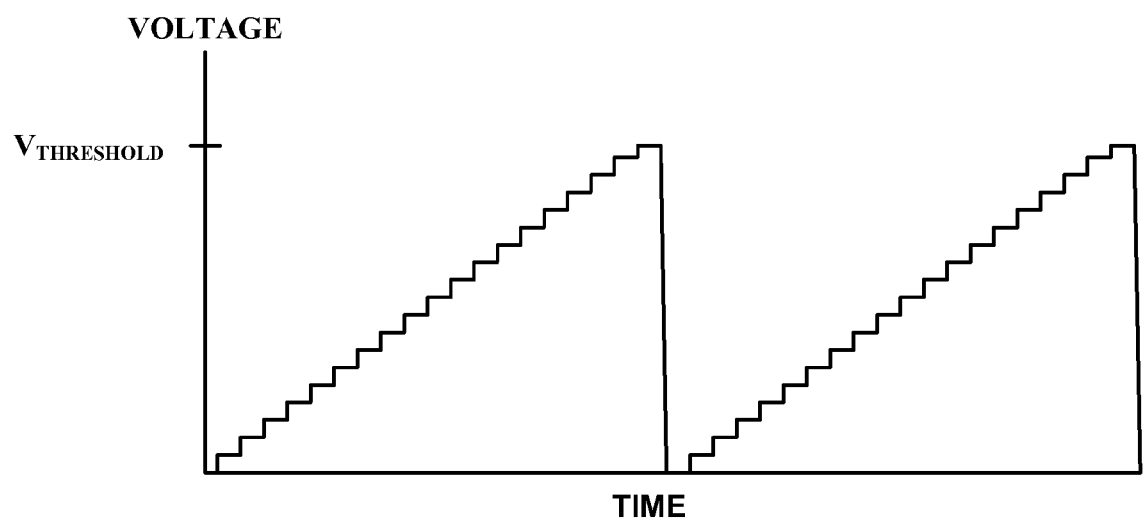
FIG. 11 is an example graph illustrating the accumulation of an integrator of the circuit of FIG. 10.

At the same time, integrator 98 begins to accumulate the voltage increments created by the detected radiation particles. Integrator 98 accumulates the incremental voltages until it reaches a threshold voltage value ($V_{threshold}$), as illustrated in FIG. 11. Each of the steps along the ramp portion of the output of integrator 98 represents an incremental voltage change caused by detection of a radiation particle. In this manner, integrator 98 may be viewed as operating as an analog counter. Upon reaching the threshold value, switch 102 is closed to drain the charge from capacitor 94.

The frequency of a timer signal output by integrator 98 may change as a function of the size of the photodiode, size of the capacitor, threshold voltage value or the like. The example circuits illustrated in FIGS. 8 and 10 are provided for purposes of illustration. Other circuits that are capable of detecting radiation particles may also be used. Additionally, integrator 98 is just one example of a type of analog counter that may be used. In other instances, integrator 98 may be replaced with a comparator that switches states upon exceeding a threshold reference voltage. Additionally, one or more digital logic elements may be used in addition to or in place of integrator 98.

In some embodiments, a digital counter (similar to digital counter 69) may be used in conjunction with radiation detection circuits 90 and 100 of FIGS. 8 and 10, respectively. The digital counter may receive the output of analog integrator 98 and increment in the case of an up counter and/or decrement in the case of a down counter when the voltage output of integrator 98 steps down. Upon reaching a threshold count value, a timer signal is generated.

Radiation detection circuits 90 and 100 may be exposed to an external source of radiation that may cause integrator 98 to reach zero or the threshold voltage sooner than desired, in turn causing an inadvertent or false timer signal. Additionally, analog integrator 98 is likely to be subject to temperature dependent leakage current errors which can cause integrator 98 to reach zero or the threshold voltage sooner than desired. In other words, the photodiode current consists of the sum of currents due to the internal radiation source, the external radiation source (if present), and a temperature dependent leakage current.

To reduce the likelihood of inadvertent or false timer signals, a second radiation detection circuit similar to those illustrated in FIGS. 8 and 10 may be placed in a location at which the photodiode of the second radiation detection circuit is unlikely to detect radiation particles from the internal radiation source, e.g., radiation source 42. Thus, the second radiation detection circuit has a photodiode current consisting of the sum of currents due to the external radiation source and the temperature dependent leakage current. The photodiode currents may be subtracted using analog current mirrors to allow radiation detection circuits 90 and 100 to account for the effects of the external radiation source and the temperature dependent leakage. Such a configuration is one possible way to measure and subtract analog currents. Other techniques also exist, such as the use of a digital subtraction module 56 as used in radiation based timer 50.

Figure 12:
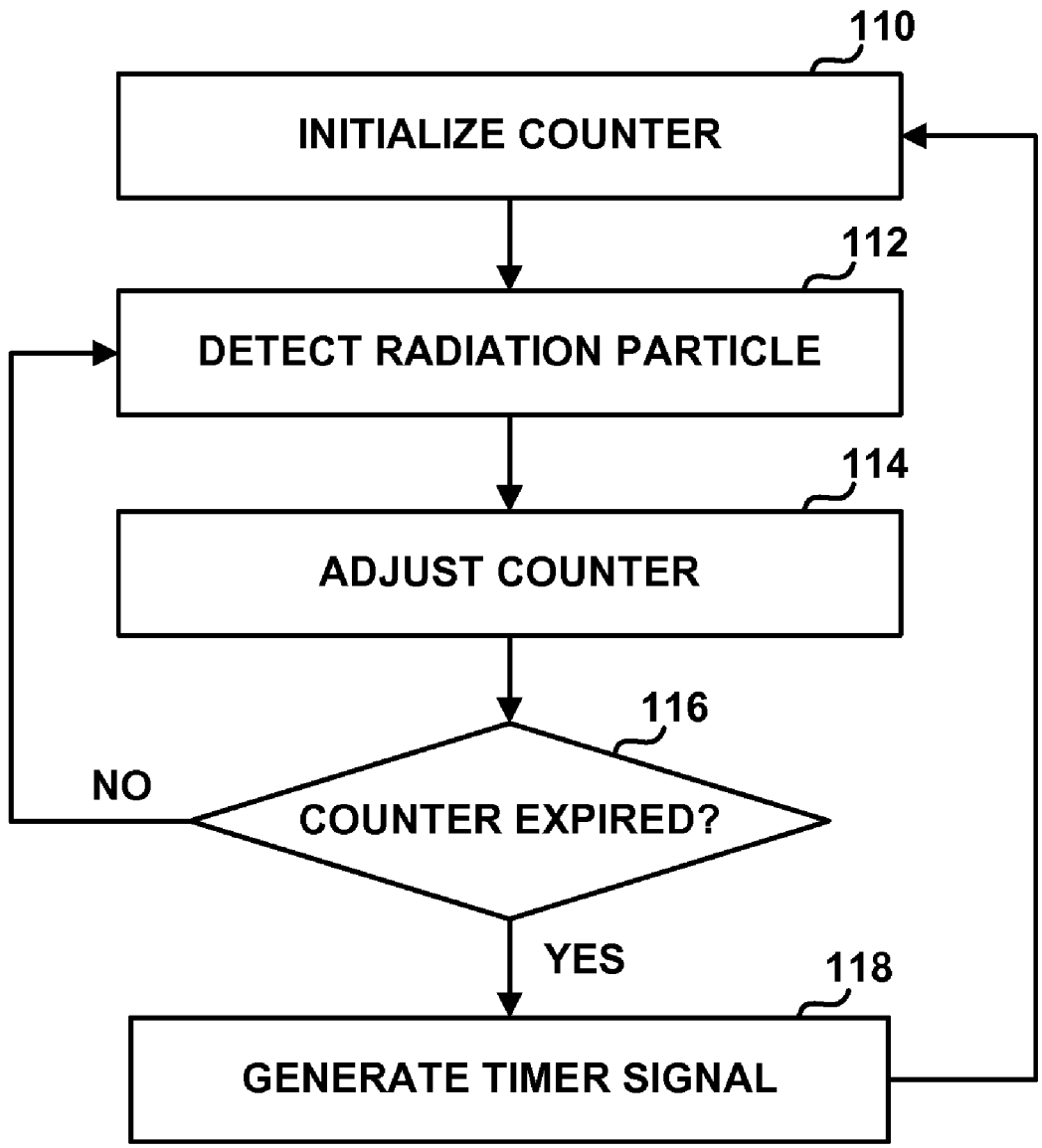
FIG. 12 is a flow diagram illustrating another example operation of a radiation-based timer generating a timer signal.

FIG. 12 is a flow diagram illustrating an example operation of a radiation-based timer, such as radiation-based timer 32, generating a timer signal. Initially, radiation-based timer 32 initializes counter 46 (110). For a digital counter, initializing counter 46 may include either setting the counter equal to zero in the case of an up counter or setting the counter equal to a threshold in the case of a down counter. For an analog counter, such as an integrator, the input of the integrator may be reset to zero volts or a threshold voltage.

One of radiation detection elements 62 detects a radiation particle (112). The radiation particle may, for example, may cause a latch to switch states or induce a current in a photodiode. In response to the detection of the radiation particle, counter 46 is adjusted (114). In the case of a digital counter, counter 46 is incremented or decremented. In the case of an integrator, the induced current or voltage is integrated to increase or decrease an output of the integrator.

Radiation-based timer 32 determines whether counter 46 has expired (116). For a digital counter, counter 46 expires when the value of counter 46 is equal to zero for a down counter or equal to the threshold for an up counter. Likewise, for an integrator, the counter is deemed to expire if the output of the integrator reaches a threshold or is equal to zero.

If the counter is not expired, radiation detection elements 62 continue to detect radiation particles. If the counter is expired, radiation-based timer 32 generates a timer signal (118). In this manner, radiation-based timer 32 generates the timer signal upon detecting a threshold number of radiation particles. The timer signal may, in some instances, be used as a wakeup trigger to periodically wakeup one or more components of IMD 20, such as telemetry module 30 or sensing module 26.

Figure 13:
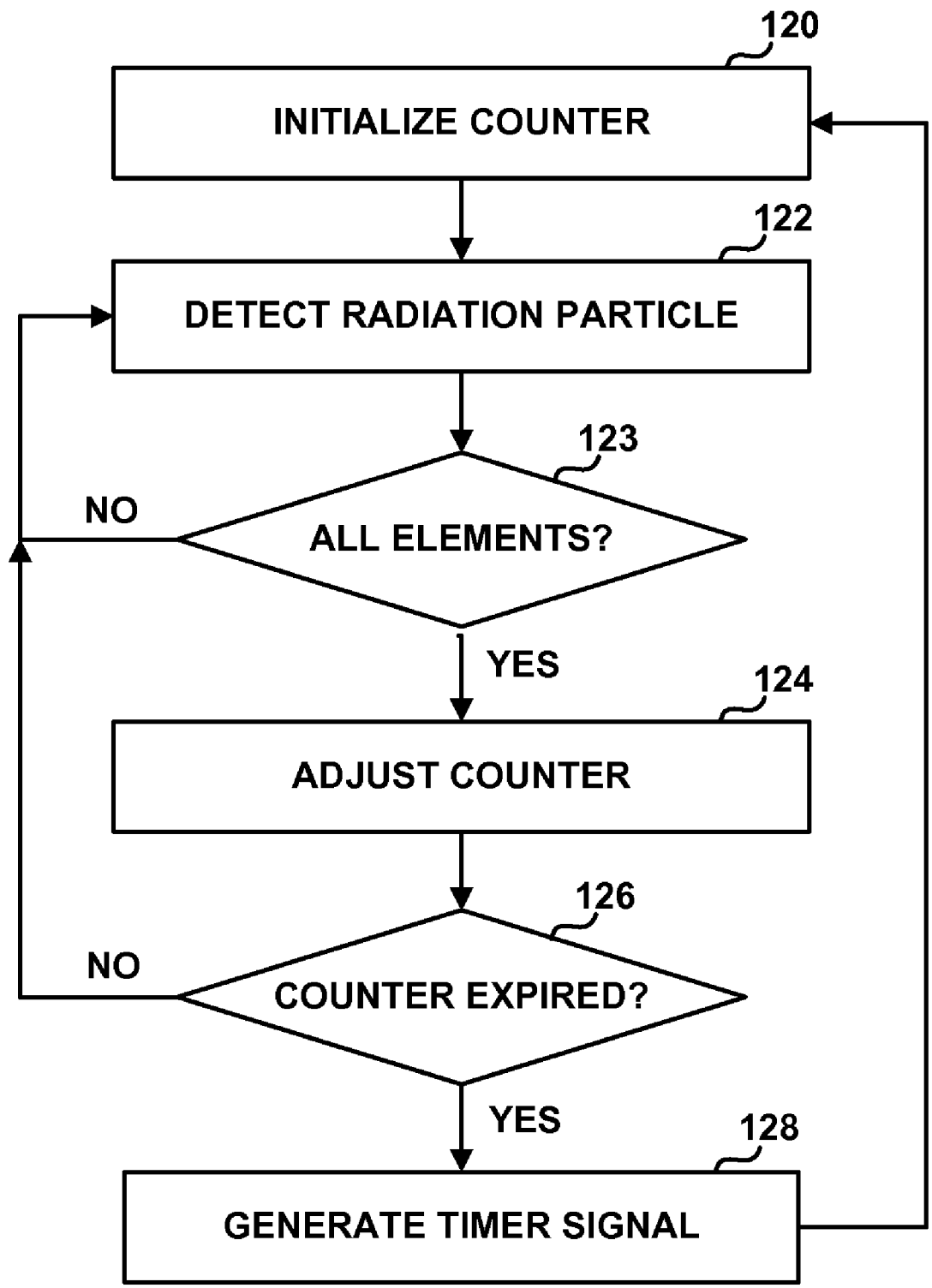
FIG. 13 is a flow diagram illustrating another example operation of a radiation-based timer generating a timer signal.

FIG. 13 is a flow diagram illustrating another example operation of a radiation-based timer, such as radiation-based timer 32, generating a timer signal. Initially, radiation-based timer 32 initializes counter 46 (120). For a digital counter, initializing counter 46 may include either setting the counter equal to zero in the case of an up counter or setting the counter equal to a threshold in the case of a down counter. For an analog counter, such as an integrator, the input of the integrator may be reset to zero volts or a threshold voltage.

One of radiation detection elements 62 detects a radiation particle (122). The radiation particle may, for example, may cause a latch to switch states or induce a current in a photodiode. Radiation-based timer 32 determines whether all of the detection elements have detected a radiation particle (123). If all of the elements have not detected a radiation particle, the counter is not adjusted and radiation-based timer waits to detect another radiation particle.

If all of the detection elements have detected a radiation particle, counter 46 is adjusted (124). In the case of a digital counter, counter 46 is incremented or decremented. In the case of an integrator, the induced current or voltage is integrated to increase or decrease an output of the integrator.

Radiation-based timer 32 determines whether counter 46 has expired (126). For a digital counter, counter 46 expires when the value of counter 46 is equal to zero for a down counter or equal to the threshold for an up counter. Likewise, for an integrator, the counter is deemed to expire if the output of the integrator reaches a threshold or is equal to zero.

If the counter is not expired, radiation detection elements 62 continue to detect radiation particles. If the counter is expired, radiation-based timer 32 generates a timer signal (128). In this manner, radiation-based timer 32 generates the timer signal upon detecting a threshold number of radiation particles. The timer signal may, in some instances, be used as a wakeup trigger to periodically wakeup one or more components of IMD 20, such as telemetry module 30 or sensing module 26.

While the preceding description has been described primarily with reference to a radiation-based timer that generates a timer signal for waking one or more components from a low power state, the radiation-based timer signal may be useful in other contexts. For example, the timer signal from the radiation-based timer may be used for performing self-testing to ensure proper function, as a watchdog timer to determine whether the device entered an unwanted state, or any other function.

The techniques described in this disclosure, including those attributed to IMD 20, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
   a radiation-based timer that includes:
   a radiation source that emits radiation particles during radioactive decay;
   at least one radiation detection element capable of detecting radiation particles; and
   a counter that tracks a number of radiation particles detected by the at least one radiation detection element, wherein the radiation-based timer generates a timer signal upon the number of detected radiation particles exceeding a threshold value;

at least one other component that uses the timer signal to perform a function;

at least one external radiation detection element that detects radiation particles emitted from an external radiation source and does not detect radiation particles emitted from the radiation source of the radiation-based timer;

a second timer that generates a second timer signal that is less affected by the external radiation source than the timer signal of the radiation-based timer, wherein the radiation-based timer determines that the timer signal is unreliable based on the external radiation detection element, and wherein the at least one other component does not use the timer signal upon the radiation-based timer determining that the timer signal is unreliable and uses the second timer signal in response to determining the timer signal of the radiation-based timer is unreliable.

2. The device of claim 1, wherein the at least one other component uses the timer signal to periodically wakeup from a low power state to perform the function.

3. The device of claim 2, wherein the at least one other component comprises a telemetry module uses the timer signal to periodically wakeup from a low power state to transmit or receive data.

4. The device of claim 2, wherein the at least one other component comprises a sensing module that uses the timer signal to periodically wakeup from a low power state to sense a physiological signal.

5. The device of claim 1, wherein:
the at least one radiation detection element comprises a plurality of radiation detection elements; and
the counter is adjusted when any one of the plurality of radiation detection elements detects a radiation particle.

6. The device of claim 1, wherein:
the at least one radiation detection element comprises a plurality of radiation detection elements; and
the counter is adjusted when each of the plurality of radiation detection elements have detected a radiation particle.

7. The device of claim 1, wherein the radiation-based timer adjusts the threshold value as a function of time based on a half-life of the radiation source.

8. The device of claim 1, wherein the radiation-based timer adjusts a value of the counter based on the radiation particles detected by the external radiation detection element.

9. The device of claim 8, wherein the counter comprises a first counter, the device further comprising:
a second counter that counts a number of radiation particles detected by the external radiation detection element,
wherein the radiation-based timer subtracts a value of the second counter from the value of the first counter to obtain a difference value and generates the timer signal when the difference value exceeds the threshold value.

10. The device of claim 1, further comprising a shield that encloses at least a portion of the radiation-based timer.

11. The device of claim 1, wherein the at least one radiation detection element comprises one of a photodiode and an inverter.

12. The device of claim 1, wherein the counter comprises one of a digital counter and an inverter.

13. The device of claim 1, wherein the radiation source comprises one or more radioactive isotopes or compounds that emit alpha particles, beta particles or gamma particles.

14. An implantable medical device comprising:
a radiation-based timer that includes:
a radiation source that emits radiation particles during radioactive decay;
at least one radiation detection element capable of detecting radiation particles; and
a counter that tracks a number of radiation particles detected by the at least one radiation detection element,
wherein the radiation-based timer generates a timer signal upon the number of detected radiation particles exceeding a threshold value;
at least one other component that uses the timer signal to perform a function; and
at least one external radiation detection element that detects radiation particles emitted from an external radiation source and does not detect radiation particles emitted from the radiation source of the radiation-based timer,
wherein the radiation-based timer determines that the timer signal is unreliable based on the external radiation detection element,
wherein the at least one other component wakes up from a low power state to a powered up state in response to determining the timer signal of the radiation-based timer is unreliable and remains in the powered up state until the timer signal of the radiation-based timer becomes reliable and does not use the timer signal upon the radiation-based timer determining that the timer signal is unreliable.

15. A method comprising:
detecting, with at least one radiation detection element, radiation particles emitted from a radiation source of a radiation-based timer during radioactive decay;
tracking a number of radiation particles detected by the at least one radiation detection element;
generating a timer signal upon the number of detected radiation particles exceeding a threshold value;
detecting radiation particles emitted from an external radiation source with an external radiation detection element that does not detect radiation particles emitted from the radiation source of the radiation-based timer;
generating a second timer signal that is less affected by the external radiation source than the timer signal of the radiation-based timer;
determining that the timer signal is unreliable based on the external radiation detection element;
using the timer signal of the radiation-based timer until it is determined that the timer signal is unreliable; and
using the second timer signal in response to determining the timer signal of the radiation-based timer is unreliable.

16. The method of claim 15, further comprising periodically waking up at least one other component of an implantable medical device from a low power state in accordance with the timer signal.

17. The method of claim 16, wherein periodically waking up at least one other component of an implantable medical device comprises periodically waking up a telemetry module from a low power state in accordance with the timer signal to transmit or receive data.

18. The method of claim 16, wherein periodically waking up at least one other component of an implantable medical device comprises periodically waking up a sensing module from a low power state in accordance with the timer signal to sense a physiological signal.

19. The method of claim 15, wherein:
detecting radiation particles comprises detecting radiation particles with a plurality of radiation detection elements; and
tracking the number of radiation particles detected comprises:
maintaining a counter; and
adjusting the counter when any one of the plurality of radiation detection elements detects a radiation particle.

20. The method of claim 15, wherein:
detecting radiation particles comprises detecting radiation particles with a plurality of radiation detection elements; and
tracking the number of radiation particles detected comprises:
maintaining a counter; and
adjusting the counter when each of the plurality of radiation detection elements has detected a radiation particle.

21. The method of claim 15, further comprising adjusting the threshold value as a function of time based on a half-life of the radiation source.

22. The method of claim 15, further comprising:
adjusting the tracked number of radiation particles detected based on the radiation particles detected by the external radiation detection element.

23. The method of claim 22, further comprising:
tracking a number of radiation particles detected by the external radiation detection element;
subtracting the tracked number of radiation particles detected by the external radiation detection element from the tracked number of radiation particles detected by the at least one radiation detection element to obtain a difference value; and
generating the timer signal when the difference value exceeds the threshold value.

24. The method of claim 15, further comprising shielding at least a portion of the radiation-based timer.

25. An implantable medical device comprising:
means for detecting radiation particles emitted from a radiation source of a radiation-based timer during radioactive decay;
means for tracking a number of radiation particles detected by the at least one radiation detection element;
means for generating a timer signal upon the number of detected radiation particles exceeding a threshold value;
means for detecting radiation particles emitted from an external radiation source with an external radiation detection element that does not detect radiation particles emitted from the radiation source of the radiation-based timer;
means for generating a second timer signal that is less affected by the external radiation source than the timer signal of the radiation-based timer;
means for determining that the timer signal is unreliable based on the external radiation detection element;
at least one component that uses the timer signal of the radiation-based timer until it is determined that the timer signal is unreliable and, in response to determining the timer signal of the radiation-based timer is unreliable, uses the second timer signal.

26. The device of claim 25, further comprising at least one other component that uses the timer signal to periodically wakeup from a low power state to perform the function.

27. The device of claim 25, further comprising means for communicating data with another device, wherein the communicating means periodically wakes up from a low power state in accordance with the timer signal to transmit or receive data.

28. The device of claim 25, further comprising means for sensing a physiological signal, wherein the sensing means periodically wakes up from a low power state in accordance with the timer signal to sense the physiological signal.

29. The device of claim 25, wherein:
the detecting means comprises a plurality of radiation detection elements; and
the tracking means comprises a counter that is adjusted when any one of the plurality of radiation detection elements detects a radiation particle.

30. The device of claim 25, wherein:
the detecting means comprises a plurality of radiation detection elements; and
the tracking means comprises a counter that is adjusted when each of the plurality of radiation detection elements have detected a radiation particle.

31. The device of claim 25, further comprising means for adjusting the threshold value as a function of time based on a half-life of the radiation source.

32. The device of claim 25, further comprising:
means for adjusting the tracked number of radiation particles to account for the radiation particles detected from the external radiation source.

33. The device of claim 25, further comprising means for shielding at least a portion of the radiation-based timer.

* * * * *